United States Patent [19]
Braun

[11] Patent Number: 6,113,392
[45] Date of Patent: Sep. 5, 2000

[54] DENTAL INSTRUMENT

[75] Inventor: Günter Braun, Holzkirchen, Germany

[73] Assignee: VDW GmbH, Munich, Germany

[21] Appl. No.: 09/288,568

[22] Filed: Apr. 9, 1999

[30] Foreign Application Priority Data

Feb. 3, 1999 [DE] Germany ............................ 199 04 289

[51] Int. Cl.[7] .................................................. A61C 3/00
[52] U.S. Cl. ............................................................ 433/141
[58] Field of Search .................................... 433/141, 102, 433/224, 147, 144; 606/85; 81/489; 16/110 R, DIG. 9; 116/307, 315; 40/913; D8/DIG. 7

[56] References Cited

U.S. PATENT DOCUMENTS

| | | | |
|---|---|---|---|
| 5,498,158 | 3/1996 | Wong | 433/102 |
| 5,519,197 | 5/1996 | Robinson et al. | 235/103 |
| 5,533,897 | 7/1996 | Zdarsky | 433/102 |

FOREIGN PATENT DOCUMENTS 44 13 804  10/1995  Germany .

*Primary Examiner*—John J. Wilson
*Assistant Examiner*—Melba Bumgarner
*Attorney, Agent, or Firm*—Nixon Peabody LLP; David S. Safran

[57] ABSTRACT

A dental instrument with an instrument part (I) and a handle part (1, 1', 1") as well as a number of countable elements (2, 2', 4) which can be individually attached to or removed from the handle part (1, 1', 1"). With each use of the instrument, the dentist is able to remove or attach one element from/to the handle part (1, 1', 1"). The number of countable elements (2, 2', 4) on the handle (1, 1', 1") provides the dentist with an indication of the number of completed uses made with the instrument, so that it can be disposed of before it is subject to stress failure during use.

9 Claims, 3 Drawing Sheets

DENTAL INSTRUMENT

BACKGROUND OF THE INVENTION

1. Field of the Invention

The invention relates to a dental instrument with an instrument part and a handle part.

2. Description of Related Art

Dental instruments, especially root canal preparation instruments, are subjected during use by the dentist to compressive, tensile, torsional and bending stresses with changing cycles, changing directions of rotation and with simultaneous movement up and down, i.e. when moved in the axial direction. Moreover, dental instruments are exposed to stresses of a chemical type from disinfectants and thermal stresses during hot sterilization. These stresses to which dental instruments are exposed leave traces on the used instruments, for example, deformation, twists by overturning, and so forth.

As result of the effects of such stresses, these instruments must be disposed of after being used only three to five times, since there is the danger that they will break if they continue to be used. To do this, it is advantageous if the dentist is able to recognize on the dental instrument how many times it has already been used and sterilized.

For a root canal preparation instrument, it is disclosed in published German Patent Application DE 4 413 804 A1 to provide a movable element on the handle part which can be moved into several discrete positions. The dentist can move the movable element after each use by one of the discrete positions and read the number of times it has been used from the respective position.

This known approach is admittedly well suited for the indicated purpose, but has the defect that it cannot be precluded that the movable element will be unintentionally moved when the instrument is being used or sterilized, so that the number of times it has been used which can be read on the respective position of the movable element is incorrect.

SUMMARY OF THE INVENTION

The primary object of the present invention is, therefore, to devise a dental instrument of the initially mentioned type on which the number of times it has been used can be recognized without error.

This object is achieved, in accordance with the invention, by countable means which can be attached to or removed or from the handle part by hand.

In the following, especially preferred embodiments of the invention are explained with reference to the accompanying drawings.

BRIEF DESCRIPTION OF THE INVENTION

DETAILED DESCRIPTION OF THE INVENTION

Figure 1:
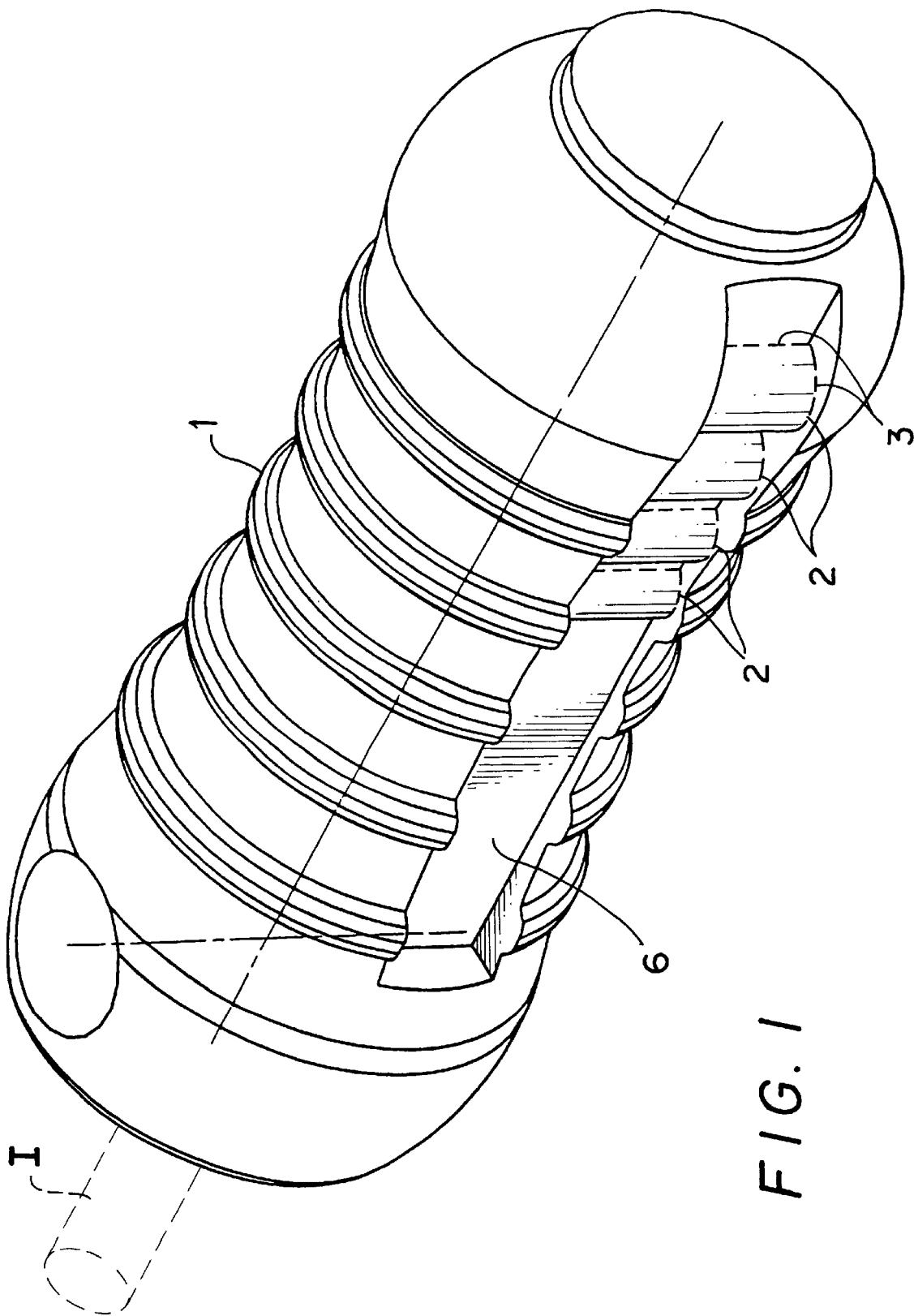
FIG. 1 is a perspective view a handle part of a first embodiment of the invention.

FIG. 1 shows a handle part 1 of a dental instrument, for example, a root canal preparation instrument in which the actual instrument part of the instrument sits. Since the type of dental instrument involved is not material to the invention, only a generic portion of the shaft of an instrument part I is represented in phantom outline in FIG. 1.

The handle part 1 shown in FIG. 1 is preferably an injection molded part made of a plastic material. In the handle part 1, in the manner shown in FIG. 1, there is a groove 6 that is axially parallel to the lengthwise direction of the handle and instrument, and in which counting elements in the form of thin plastic fins or plates 2 plates 2, that are inclined in the longitudinal direction of the handle part, are injected. These plastic elements 2 have scored sites 3 on the side edges where they meet the walls of the groove 6 of the handle part 1.

The number of plastic elements 2 corresponds to no more than the maximum number of allowable uses of the dental instrument. After one use of the instrument by the dentist or after sterilization, for example, using tweezers, one of the plastic counting elements 2 can be broken off. Thus, by counting the remaining counting elements 2 and finding the difference from the original number of fins 2 the number of times that the instrument has been used can be determined, and maximum remaining number of uses can be seen at a glance.

Figure 2:
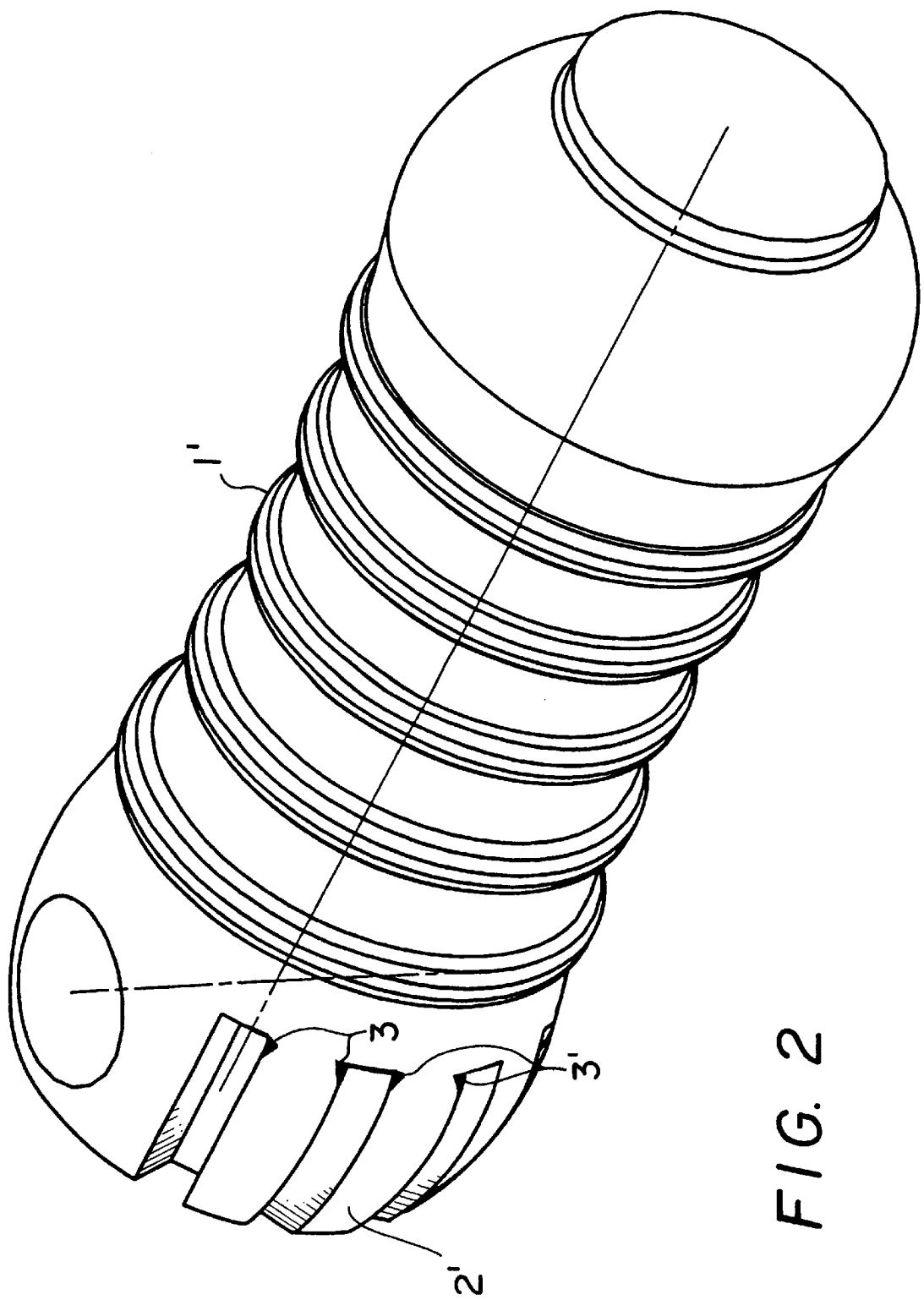
FIG. 2 is a perspective view of the handle part according to second embodiment.

FIG. 2 shows a second embodiment of a handle part 1' for a dental instrument in which the counting elements 2' which would enable the dentist to recognize how often the instrument has already been used are made in the form of small thin element 2 which are injected or cast onto one of the axial ends of the handle part 1', in the embodiment shown in FIG. 2, onto the upper end of the handle part 1'.

In the second embodiment, the counting elements 2' have scored sites 3' located on the side and on the end of their base. Preferably, the fin-shaped counting elements 2' run parallel to the axial direction of the handle part 1.

After using the instrument, a fin is removed, i.e. broken off, so that it becomes recognizable via the remaining number of fins how often the instrument has already been used/can still be used.

Figure 3:
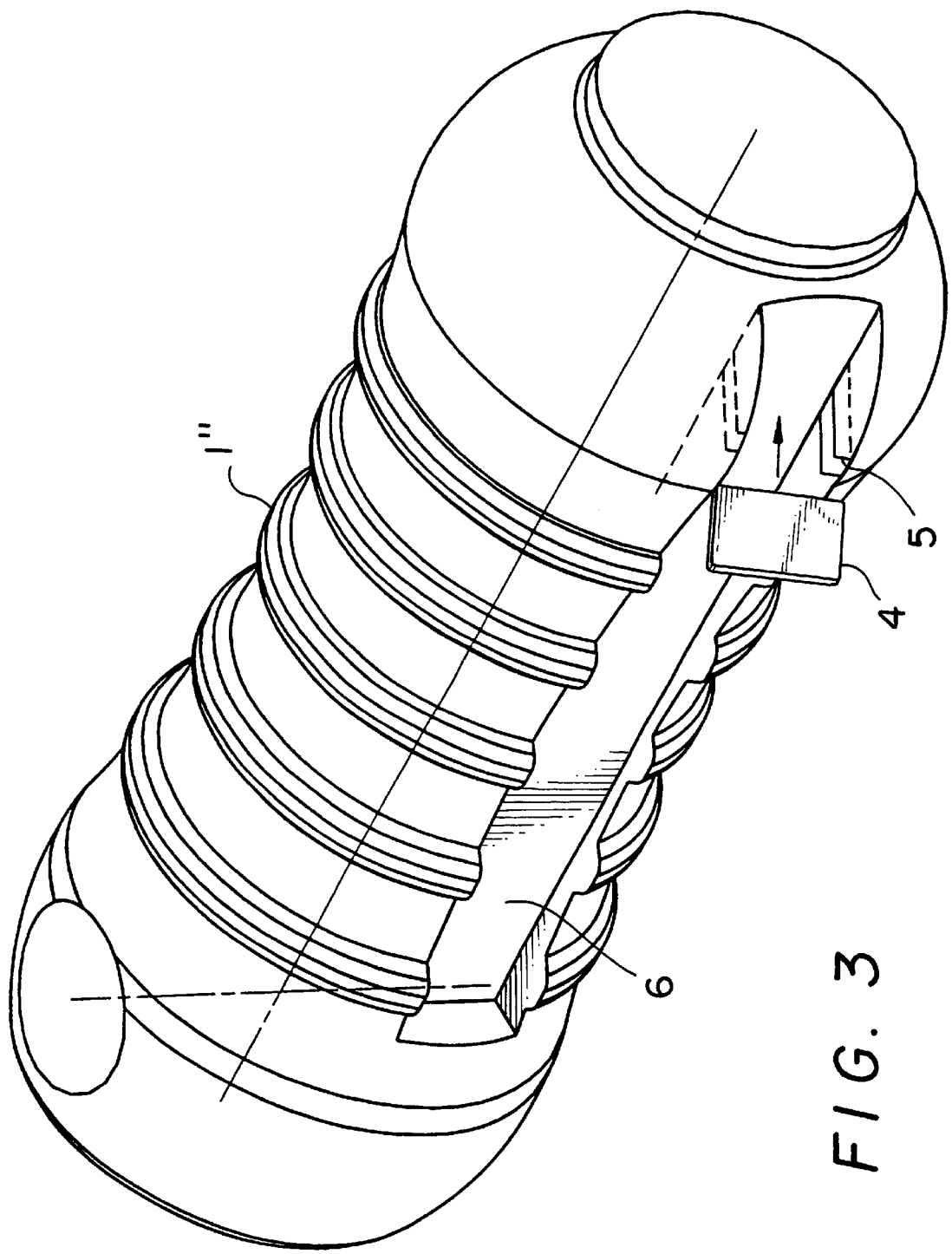
FIG. 3 is a perspective view of the handle part of a third embodiment of the invention.

The third embodiment, which is shown in FIG. 3, differs from the first two embodiments of FIGS. 1 & 2 in that the counting elements which indicate how often the instrument has already been used does not comprise elements which are separated from the handle part. Instead, the counting elements are parts which are attached to the handle part after each use.

As is shown in FIG. 3, to do this, the handle part 1" has an axial groove 6 similar to that of the first embodiment. However, in this groove 6 there are small guide channels 5 into which, for example, small plastic or metal plates 4 can be inserted. When the dentist inserts a small plastic or metal plate 4 into one of the guide channel 5 after each use, by counting the small plastic or metal plates 4 located on the handle part it can be recognized how often the instrument has already been used. In this regard, while only a single pair of guide channels 5 is shown, a number of them would be similarly positioned to the locations of the elements 2 in the FIG. 1 embodiment.

The design in accordance with the invention has the advantage that the number of uses of the instrument is not read using the position of an individual movable element which can become inadvertently repositioned, but instead the number of uses of the instrument is determined by counting the number of individual elements located in the handle part. Unintentional movement is thus precluded.

I claim:

1. Dental instrument with an instrument part and a handle part, characterized by countable means for determining when the useful life of the instrument has been reached, said countable means comprising a set of countable elements equal to a predetermined number of uses for the instrument, the number of countable elements attached to the handle part being changeable by hand; wherein the countable elements are detachably attached to the handle part in a manner enabling the countable elements to be individually detached from the handle part after each use of the instrument; and wherein the handle part is made of a plastic material and the individually detachable, countable elements are molded on to the handle part.

2. Dental instrument as claimed in claim 1, wherein the individually detachable, countable elements are made in the form of plastic ribs, fins or plates.

3. Dental instrument as claimed in claim 2, wherein the countable elements are connected to the handle part by scored sites.

4. Dental instrument as claimed in claim 2, wherein an axial groove is provided in the handle part parallel to a longitudinal axis thereof; and wherein the individually detachable, countable elements are mounted within said axial groove.

5. Dental instrument as claimed in claim 4, wherein the countable elements are connected to the handle part by scored sites.

6. Dental instrument as claimed in claim 5, wherein the plastic fins are inclined in the longitudinal direction of the handle part.

7. Dental instrument as claimed in claim 2, wherein the plastic fins are located at an end of the handle part.

8. Dental instrument as claimed in claim 7, wherein the countable elements are connected to the handle part by scored sites.

9. Dental instrument with an instrument part and a handle part, characterized by countable means for determining when the useful life of the instrument has been reached, said countable means comprising a set of countable elements equal to a predetermined number of uses for the instrument, the number of countable elements attached to the handle part being changeable by hand; wherein the handle part is provided with a respective receiver for each of the countable elements, so that a countable element is insertable into the respective receiver in the handle part after each use of the instrument; wherein an axial groove is provided in the handle part parallel to a longitudinal axis thereof; wherein each receiver is formed of slots provided in walls bounding the axial groove; and wherein the countable elements are in the form of small plates.

\* \* \* \* \*